United States Patent [19]
Cross et al.

[11] Patent Number: 5,057,528
[45] Date of Patent: Oct. 15, 1991

[54] AMINO-PYRIDINE COMPOUNDS USEFUL AS ANTI-ARRHYTHMIC AGENTS

[75] Inventors: Peter E. Cross; Roger P. Dickinson, both of New York, N.Y.

[73] Assignee: Pfizer Inc., New York, N.Y.

[21] Appl. No.: 572,081

[22] Filed: Aug. 23, 1990

Related U.S. Application Data

[62] Division of Ser. No. 393,423, Aug. 14, 1989, Pat. No. 4,968,704.

[30] Foreign Application Priority Data

Aug. 13, 1988 [GB] United Kingdom ............... 8819307

[51] Int. Cl.$^5$ .................... C07D 213/74; A61K 31/44
[52] U.S. Cl. ................................... 514/352; 546/307; 546/308; 546/309; 546/311; 546/312
[58] Field of Search ............... 546/307, 311, 312, 308, 546/309; 514/352

[56] References Cited

FOREIGN PATENT DOCUMENTS 0013408  7/1980  European Pat. Off. ............ 546/281
0244115 11/1987  European Pat. Off. ............ 544/536
0245997 11/1987  European Pat. Off. ............ 564/567

*Primary Examiner*—C. Warren Ivy
*Assistant Examiner*—Zinna Northington-Davis
*Attorney, Agent, or Firm*—Peter C. Richardson; Paul H. Ginsburg

[57] ABSTRACT

A series of novel aryloxyalkylamino - and arylaminoalkylamino-pyridine and imidazole compounds have been prepared, including their pharmaceutically acceptable salt, wherein the aryl moiety is further substituted by a sulphamoyl or sulphonylamino group or by a ureido or acylamino group located at the para-position of the ring with respect to the aforesaid alkylamino side chain. These compounds are useful in therapy as anti-arrhythmic agents and therefore, are of value in the treatment of various cardiac arrhythmias. Methods for preparing all these compounds from know starting materials are provided.

11 Claims, No Drawings

AMINO-PYRIDINE COMPOUNDS USEFUL AS ANTI-ARRHYTHMIC AGENTS

This is a division of application Ser. No. 07/393,423, filed on Aug. 14, 1989, now U.S. Pat. No. 4,968,704.

BACKGROUND OF THE INVENTION

This invention relates to antiarrhythmic agents useful in the treatment of cardiac arrhythmias.

The compounds of the invention prolong the duration of the action potential in cardiac muscle and conducting tissue, and thereby increase refractoriness to premature stimuli. Thus, they are Class III antiarrhythmic agents according to the classification of Vaughan Williams (Antiarrhythmic Action, E. M. Vaughan Williams, Academic Press, 1980). They are effective in atria, ventricles and conducting tissue both in vitro and in vivo and are therefore useful for the prevention and treatment of a wide variety of ventricular and supraventricular arrhythmias including atrial and ventricular fibrillation. Because they do not alter the speed at which impulses are conducted, they have less propensity than current drugs (mostly Class I) to precipitate or aggravate arrhythmias, and they also produce less neurological side effects. Some of the compounds also have positive inotropic activity and therefore are particularly beneficial in patients with impaired cardiac pump function.

SUMMARY OF THE INVENTION

The invention provides antiarrhythmic agents of the formulae:

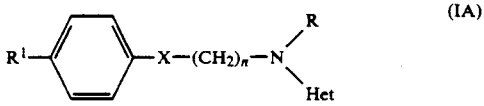

(IA)

and

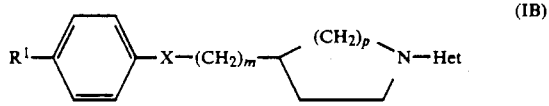

(IB)

and their pharmaceutically acceptable salts, wherein
X is O or N—($C_1$-$C_4$ alkyl);
R is $C_1$-$C_4$ alkyl;
$R^1$ is $R^2SO_2NH$— or $R^2CONH$—,
  wherein $R^2$ is $C_1$-$C_4$ alkyl, $C_3$-$C_7$ cycloalkyl or $R^3R^4N$—,
    wherein $R^3$ and $R^4$ are each independently selected from H and $C_1$-$C_4$ alkyl;
"Het" is either (a) 2-, 3- or 4-pyridyl optionally substituted by 1 or 2 substituents, each independently selected from —$NH_2$ and $C_1$-$C_4$ alkyl, or (b) 2-imidazolyl optionally substituted by 1 or 2 $C_1$-$C_4$ alkyl groups;
m is 0, 1 or 2;
n is 2, 3 or 4; and
p is 1 or 2.

$C_3$ and $C_4$ alkyl groups may be straight or branched chain.

Preferably, the $C_1$-$C_4$ alkyl group is methyl.
Preferably, $R^1$ is $CH_3SO_2NH$—.
Preferably, "Het" is 2-, 3- or 4-pyridyl which may be optionally substituted by 1 or 2 substituents each independently selected from —$NH_2$ and $C_1$-$C_4$ alkyl.
Most preferably, "Het" is 4-pyridyl.
Preferably, m is 0 or 1.
Preferably, n is 2.
Preferably, p is 2.

The pharmaceutically acceptable salts of the compounds of the formulae (IA) and (IB) include acid addition salts formed from acids which form non-toxic salts such as the hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, benzenesulphonate and p-toluenesulphonate salts.

Some of the compounds, e.g. those in which $R^1$ is $R^2SO_2NH$—, may also form metal salts, particularly alkaline earth and alkali metal salts. Examples include the sodium and potassium salts.

Particularly preferred individual compounds are N-[4-(N'-Methyl-N'-[2-(N''-methyl-N''-[4-pyridyl-]amino)ethyl]amino)phenyl]methanesulphonamide and
N-[4-([1-(4-Pyridyl)piperidin-4-yl]methoxy)phenyl]methanesulphonamide, together with pharmaceutically acceptable salts thereof.

DETAILED DESCRIPTION OF THE INVENTION

The compounds of the formula (IA) or (IB) provided by the invention may be prepared by the following methods:

(1) Preferably, the compounds of the formula (IA) or (IB), wherein "Het" is pyridyl or pyridyl substituted by $C_1$-$C_4$ alkyl, and X, R, $R^1$, m, n and p are as defined for formulae (IA) and (IB), are prepared from intermediates of the formula:

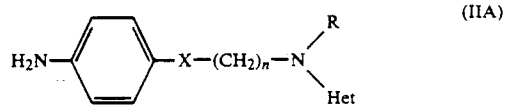

(IIA)

or

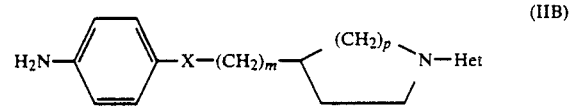

(IIB)

wherein "Het" is pyridyl or pyridyl substituted by $C_1$-$C_4$ alkyl and X, R, m, n and p are as defined for formulae (IA) and (IB).

The compounds of the formula (IA) or (IB), wherein "Het", X, R, m, n and p are as defined for the formula (IIA) and (IIB) and $R^1$ is
a) $R^2SO_2NH$—,
wherein $R^2$ is $C_1$-$C_4$ alkyl, $C_3$-$C_7$ cycloalkyl or $R^3R^4N$—, wherein $R^3$ is H or $C_1$-$C_4$ alkyl and $R^4$ is $C_1$-$C_4$ alkyl, can be prepared by reacting a compound of the formula (IIA) or (IIB) with a sulphonyl halide of the formula ($C_1$-$C_4$ alkyl or $C_3$-$C_7$ cycloalkyl)$SO_2$(Cl or Br), a sulphonic anhydride of the formula ([$C_1$-$C_4$ alkyl or $C_3$-$C_7$ cycloalkyl]$SO_2)_2O$ or with a sulphamoyl chloride of the formula $R^3R^4NSO_2Cl$, wherein $R^3$ is H or $C_1$-$C_4$ alkyl and $R^4$ is $C_1$-$C_4$ alkyl, in the presence of a suitable acid acceptor, e.g. triethylamine or pyridine. The reaction is typically carried out at from 0° C. to room temperature in a suitable organic solvent, e.g. methylene chloride. Preferably, the reaction is carried out using pyridine as both the solvent and the acid acceptor at room temperature;

b) $H_2NSO_2NH-$, can be prepared by reacting a compound of the formula (IIA) or (IIB) with sulphamide at up to, and preferably at, the reflux temperature in a suitable organic solvent, e.g. 1,4-dioxane;

c) $R^2CONH-$, wherein $R^2$ is $C_1-C_4$ alkyl or $C_3-C_7$ cycloalkyl, can be prepared by acylating a compound of the formula (IIA) or (IIB) with either an acid halide of the formula ($C_1-C_4$ alkyl or $C_3-C_7$ cycloalkyl)CO(Cl or Br) or with an acid anhydride of the formula ([$C_1-C_4$ alkyl or $C_3-C_7$ cycloalkyl]CO)$_2$O. When an acid halide is employed the reaction is typically carried out from 0° C. to room temperature in a suitable organic solvent, e.g. methylene chloride, and in the presence of a suitable acid acceptor, e.g. triethylamine or pyridine. The reaction may also be carried out using pyridine as both the solvent and the acid acceptor. When an acid anhydride is employed the reaction is typically carried out at up to the reflux temperature, preferably at 100° C., in a suitably compatible organic solvent, e.g. a carboxylic acid of the formula ($C_1-C_4$ alkyl or $C_3-C_7$ cycloalkyl)-COOH;

d) $H_2NCONH-$, can be prepared by reacting a compound of the formula (IIA) or (IIB) with sodium or potassium cyanate at up to, and preferably at the reflux temperature under acidic conditions, e.g. in aqueous acetic acid;

e) ($C_1-C_4$ alkyl)NHCONH—, can be prepared by reacting a compound of the formula (IIA) or (IIB) with a $C_1-C_4$ alkyl isocyanate. The reaction is preferably carried out at room temperature in a suitable organic solvent, e.g. dimethylformamide, although if necessary elevated temperatures may be employed to accelerate the rate of reaction, or f) ($C_1-C_4$ alkyl)$_2$NCONH—, can be prepared by reacting a compound of the formula (IIA) or (IIB) with a compound of the formula ($C_1-C_4$ alkyl)$_2$NCOCl. The reaction is typically carried out at from 0° C. to the reflux temperature in a suitable organic solvent, e.g. methylene chloride, and in the presence of a suitable acid acceptor, e.g. triethylamine or pyridine.

(2) The compounds of the formula (IA) or (IB), wherein "Het", X, R, $R^1$, m, n and p are as defined for formulae (IA) and (IB), can be prepared from intermediates of the formula:

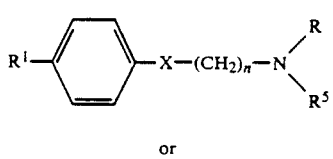

(IIIA)

or

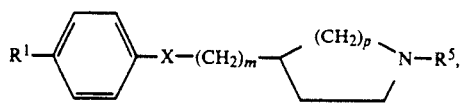

(IIIB)

wherein X, R, $R^1$, m, n and p are as defined for formulae (IA) and (IB), and $R^5$ is either H or

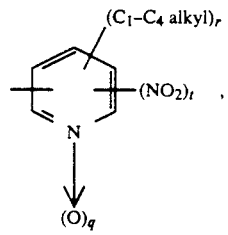

wherein q is 0 or 1, r is 0 or 1 and t is 1 or 2, with the proviso that the sum of r and t is 1 or 2.

The compounds of the formula (IA) or (IB), wherein X, R, $R^1$, m, n and p are as defined for formulae (IA) and (IB) and "Het" is a) pyridyl or pyridyl substituted by $C_1-C_4$ alkyl, can be prepared by reacting a compound of the formula (IIIA) or (IIIB), wherein $R^5$ is H, with a halopyridine of the formula

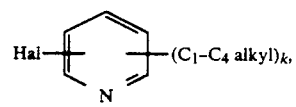

wherein "Hal" is halo, preferably Cl or Br, and k is 0, 1 or 2. The reaction is typically carried out at up to, and preferably at the reflux temperature in a suitable organic solvent, e.g., n-butanol or amyl alcohol, and in the presence of a suitable acid acceptor, e.g. sodium carbonate or sodium bicarbonate;

b) pyridyl substituted by —NH$_2$ and optionally by $C_1-C_4$ alkyl, can be prepared by reduction of a compound of the formula (IIIA) or (IIIB), wherein $R^5$ is

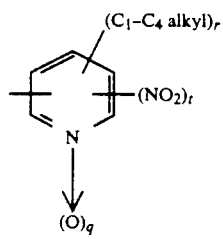

wherein q, r and t are as defined for formulae (IIIA) and (IIIB), by conventional methods. Preferably, the reduction is carried out by catalytic hydrogenation using a suitable catalyst, e.g. palladium on charcoal, at room temperature and in a suitable inert organic solvent, e.g. ethanol; or c) 2-imidazolyl or 2-imidazolyl substituted by $C_1-C_4$ alkyl, can be prepared from a compound of the formula (IIIA) or (IIIB), wherein $R^5$ is H, according to the appropriate following scheme 1 or 2:

Scheme 1
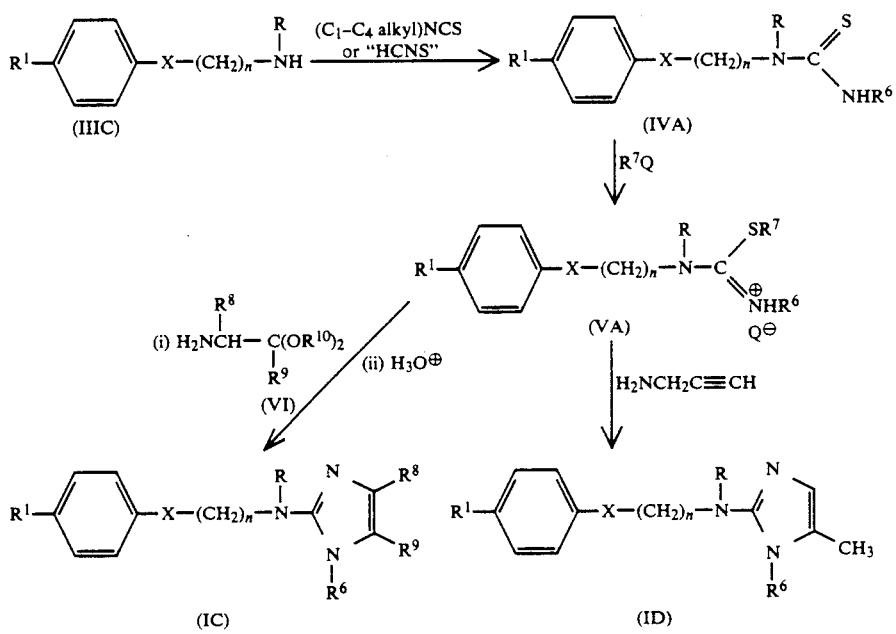
Scheme 2
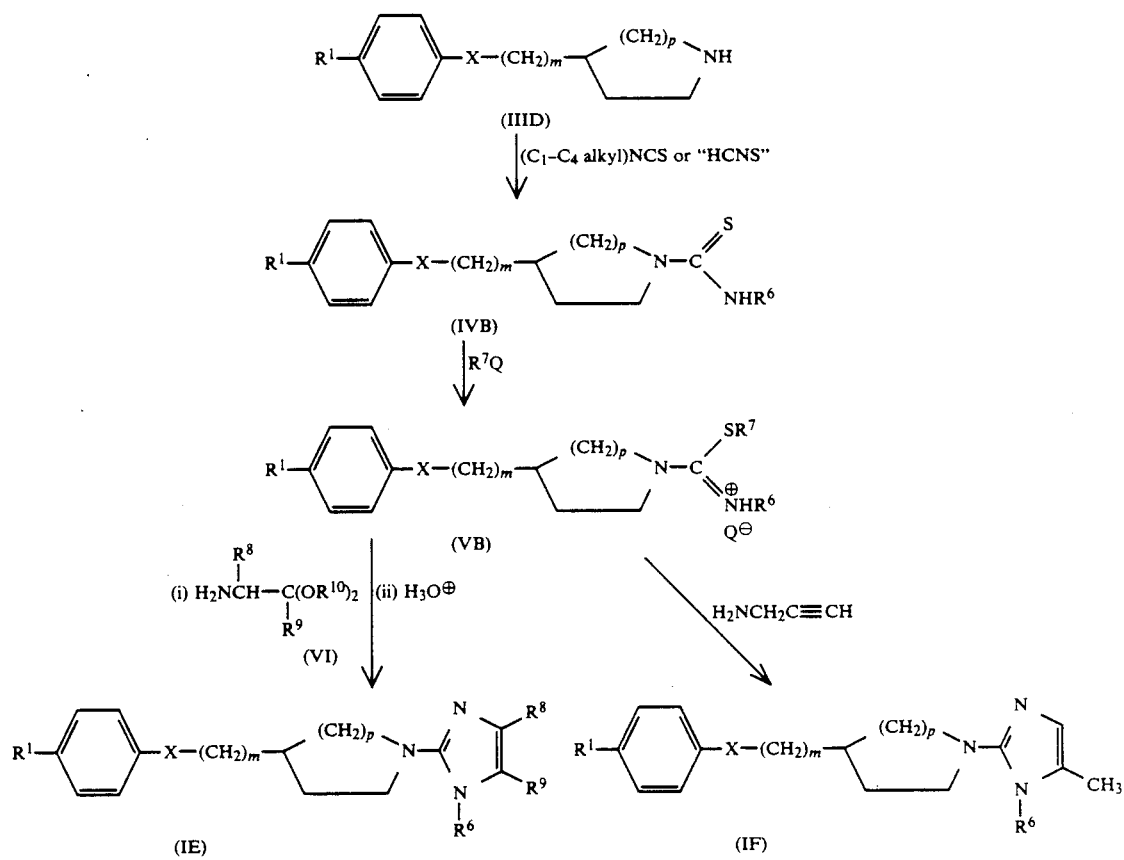
wherein $R^6$ is H or $C_1$-$C_4$ alkyl, $R^7$ is $C_1$-$C_4$ alkyl, $R^8$ and $R^9$ are each independently H or $C_1$-$C_4$ alkyl, each $R^{10}$ is $C_1$-$C_4$ alkyl or the two groups $R^{10}$ are joined to form a $C_2$-$C_3$ alkylene chain, and Q is preferably halo (preferably iodo), ($C_1$-$C_4$ alkyl)$SO_3$—,

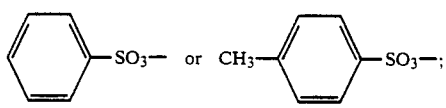

with the proviso that not more than two of $R^6$, $R^8$ and $R^9$ in formulae (IC) and (IE) are $C_1$-$C_4$ alkyl.

In the first step, a compound of the formula (IIIC) or (IIID) is either (a) reacted with a $C_1$-$C_4$ alkyl isothiocyanate in a suitable organic solvent, e.g. methanol or dichloromethane, at about room temperature to give a carbothioamide (IVA) or (IVB), wherein $R^6$ is $C_1$-$C_4$ alkyl, or (b) reacted with a thiocyanate salt, e.g. ammonium, sodium or potassium thiocyanate, under acidic conditions to give a carbothioamide in which $R^6$ is H.

The carbothiamide is then S-alkylated, preferably using a $C_1$-$C_4$ alkyl halide (preferably an iodide) or a compound of the formula ($C_1$-$C_4$ alkyl)$SO_3R^7$, The S-alkyl derivative (VA) or (VB) can then be converted to an imidazole by two different methods.

In the first method, the S-alkyl derivative is reacted with the acetal (VI), e.g. by heating at from 60°-130° C. and preferably under reflux in a suitable organic solvent (such as pyridine), to form an intermediate guanidine. The guanidine is then heated in aqueous acid, e.g. aqueous hydrochloric acid, and preferably under reflux, to cyclise it to the product (IC) or (IE).

In the second method, the S-alkyl derivative is converted to the imidazole (ID) or (IF) by reaction with propargylamine in a suitable organic solvent, e.g. pyridine, and typically at a temperature of from 60°-130° C. and preferably under reflux.

The intermediates of the formula (IIA), (IIB), (IIIA) or (IIIB) required for the preparation of the compounds of the invention of the formula (IA) or (IB) may be prepared by the following methods:

(1) The intermediates of the formulae (IIA) and (IIB), wherein "Het", X, R, m, n, and p are as previously defined for the formulae (IIA) and (IIB), can be prepared by conventional techniques, e.g. as described in Preparations 1 to 4 of the Preparations section, as summarised by the following scheme:

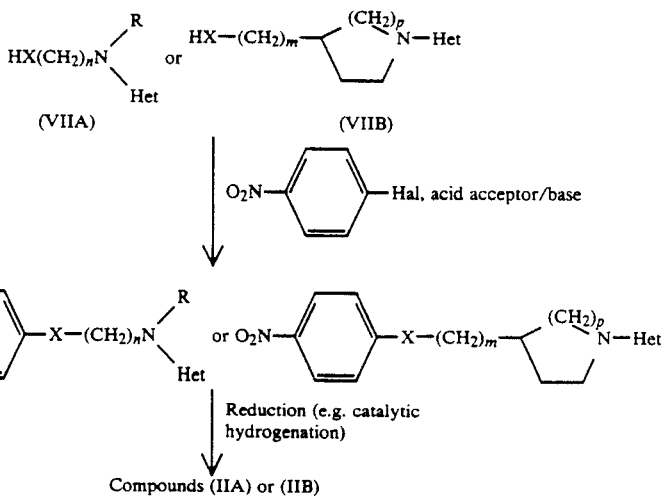

wherein "Hal" is halo, preferably F, Cl or Br.

The starting materials a) of the formulae (VIIA) and (VIIB), wherein X is 0, and the compounds of the formula (VIIA), wherein X is N—($C_1$-$C_4$ alkyl), wherein the said $C_1$-$C_4$ alkyl group is identical to that selected for R in the formula (IIA), can be prepared by conventional techniques, e.g. as described in Preparations 1 to 4 of the Preparations section; or b) of the formulae (VIIA) and (VIIB), wherein X is N—($C_1$-$C_4$ alkyl), may be prepared by conventional techniques according to the following scheme:

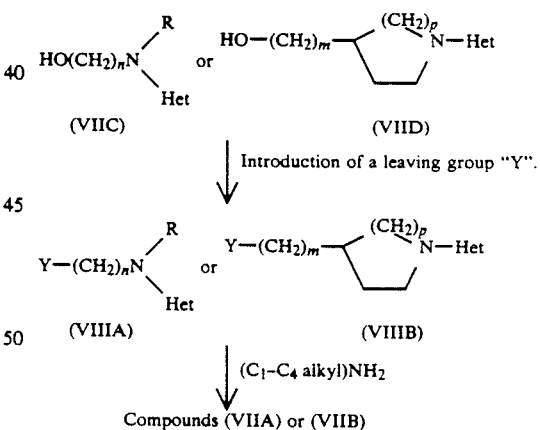

wherein Y is a suitable leaving group, e.g. methanesulphonyloxy or halo, preferably Cl or Br.

In a typical procedure, a suitable leaving group "Y" is introduced into a compound of the formula (VIIC) or (VIID) (prepared according to part (a)) by conventional methods, e.g. thionyl chloride or bromide; or methanesulphonyl chloride or methanesulphonic anhydride in the presence of an acid acceptor, to give a compound of the formula (VIIIA) or (VIIIB) which may be reacted with a ($C_1$-$C_4$ alkyl)amine by conventional techniques (e.g. using a 2-10 fold excess of the amine in an inert solvent, if necessary in a suitable "pressure vessel") to give a compound of the formula (VIIA) or (VIIB).

(2) The intermediates of the formulae (IIIA) and (IIIB), wherein X, R, $R^1$, m, n and p are as previously defined for the formulae (IIIA) and (IIIB) and $R^5$ is H, can be prepared by conventional techniques, e.g. as described in Preparation 5 of the Preparations section, as summarised in the following scheme:

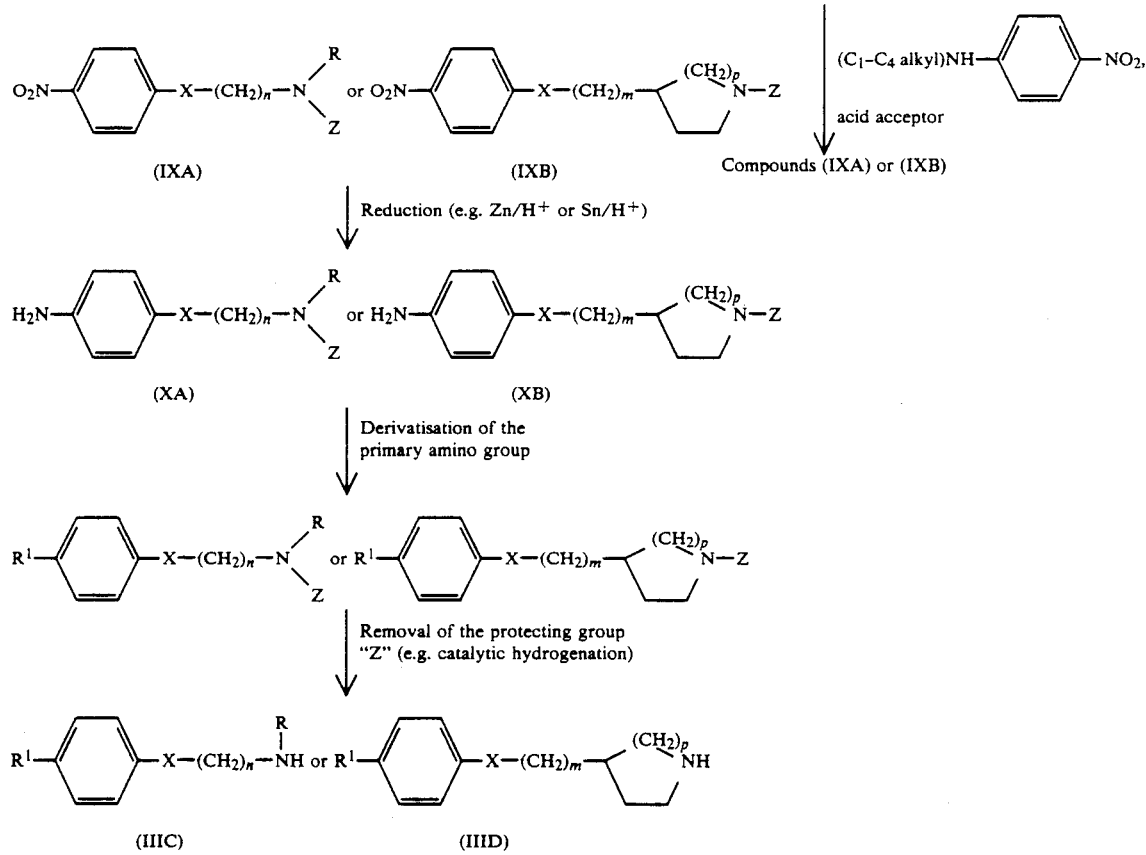

wherein Z is a suitable protecting group, e.g. benzyloxycarbonyl or benzyl.

Derivatisation of a compound of the formula (XA) or (XB) may be accomplished by conventional procedures similar to those previously described in Method 1 for the preparation of the compounds of the formulae (IA) and (IB).

The starting materials a) of the formulae (IXA) and (IXB), wherein X is O, and the compounds of the formula (IXA), wherein X is $N—(C_1-C_4\,alkyl)$, wherein the said $C_1-C_4$ alkyl group is identical to that selected for R in the formula (IIIA), can be prepared by conventional techniques, e.g. as described in the Preparations section, in particular as in Preparation 5; or b) of the formulae (IXA) and (IXB), wherein X is $N—(C_1-C_4\,alkyl)$, may be prepared by conventional techniques according to the following scheme:

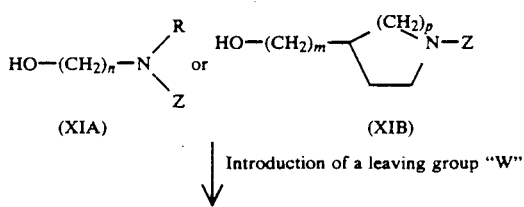

wherein Z is a suitable protecting group, e.g. benzyloxycarbonyl or benzyl and W is a suitable leaving group, e.g. methanesulphonyloxy or halo (preferably Cl or Br).

In a typical procedure, a suitable leaving group "W" is introduced into a compound of the formula (XIA) or (XIB) (prepared according to part (a)) by conventional methods, e.g. carbon tetrachloride or tetrabromide/triphenylphosphine; or methanesulphonyl chloride or methanesulphonic anhydride in the presence of an acid acceptor, to give a compound of the formula (XIIA) or (XIIB), that may be reacted with an amine of the formula:

$(C_1-C_4\,alkyl)NH$—⟨phenyl⟩—$NO_2$ by conventional techniques, e.g. in the presence of a suitable acid acceptor such as $Na_2CO_3$ and in a suitable organic solvent, to give a compound of the formula (IXA) or (IXB).

(3) The intermediates of the formula (IIIA) or (IIIB), wherein X, R, R¹, m, n and p are as defined for formulae (IIIA) and (IIIB) and R⁵ is

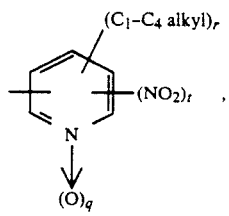

wherein q, r and t are as previously defined for the formulae (IIIA) and (IIIB), can be prepared by reacting a compound of the formula (IIIA) or (IIIB), wherein R⁵ is H, with a halopyridine of the formula:

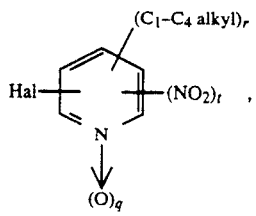

wherein "Hal" is halo, preferably Cl or Br, and q, r and t are as previously defined for the formulae (IIIA) and (IIIB).

The reaction is typically carried out in the presence of a suitable acid acceptor, e.g. NaHCO$_3$, and at up to the reflux temperature, preferably under reflux, in a suitable organic solvent, e.g. n-butanol. The reaction may also be carried out using pyridine as both the solvent and the acid acceptor.

The invention also includes any novel intermediates disclosed herein, such as those of the formulae (IIA), (IIB), (IIIA) and (IIIB).

All of the above reactions are conventional, and appropriate reagents and reaction conditions for their performance and procedures for isolating the desired products will be well known to those skilled in the art in accordance with literature precedents and by reference to the Examples hereto.

Pharmaceutically acceptable salts are readily prepared by mixing solutions containing equimolar amounts of the free base and the desired acid. The salt generally precipitates from solution or is recovered by evaporation of the solvent.

The biological activity of the compounds of the invention is assessed by measuring the effect of the compounds on atrial refractoriness. In this test guinea pig right hemiatria are mounted in a bath containing physiological salt solution, with one end connected to a force transducer. The tissues are stimulated at 1 Hz using field electrodes. Effective refractory period (ERP) is measured by introducing premature stimuli (S$_2$) after every 8th basic stimulus (S$_1$). The S$_1$S$_2$ coupling interval is gradually increased until S$_2$ reproducibly elicits a propagated response. This is defined as the ERP. The test compound is then added to the bath and the concentration of compound required to increase ERP by 25% is determined (ED$_{25}$). ERP is also measured in guinea pig right papillary muscles incubated in physiological saline solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artefact and the peak of the electrogram (i.e. the time required for the impulse to travel along the length of the muscle).

Atrial and ventricular ERP's are also measured in anaesthetised or conscious dogs by the extrastimulus technique whilst the atrium or right ventricle is being paced at a constant rate.

For human use the compounds of the formulae (IA) or (IB) can be administered alone but will generally be administered in admixture with a pharmaceutical carrier selected with regard to the intended route of administration and standard pharmaceutical practice. They can be administered both to patients suffering from arrhythmias and also, prophylactically, to those likely to develop arrhythmias. For example, they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic with blood.

For administration to man in the curative or prophylactic treatment of cardiac conditions such as ventricular and supraventricular arrhythmias, including atrial and ventricular fibrillation, it is expected that oral dosages of the compounds of the invention will be in the range from 1 to 75 mg daily, taken in up to 4 divided doses per day, for an average adult patient (70 kg). Thus for a typical adult patient, individual tablets or capsules might contain 1 to 25 mg of active compound, in a suitable pharmaceutically acceptable vehicle or carrier. Dosages for intravenous administration would be expected to be within the range 0.5 to 10 mg per single dose as required. A severe cardiac arrhythmia is preferably treated by the i.v. route in order to effect a rapid conversion to the normal rhythm. Variations on these dosages may occur depending on the weight and condition of the subject being treated as will be determined by the medical practitioner.

Thus the present invention provides a pharmaceutical composition comprising a compound of the formula (IA) or (IB), as defined above, or a pharmaceutically acceptable salt thereof, together with a pharmaceutically acceptable diluent or carrier.

The invention also provides a method of preventing or reducing cardiac arrhythmias in a human being, which comprises administering to said human being an effective amount of a compound of the formula (IA) or (IB), or a pharmaceutically acceptable salt thereof, or of a pharmaceutical composition as defined above.

The invention yet further provides a compound of the formula (IA) or (IB), or a pharmaceutically acceptable salt thereof, for use as a medicament, in particular as an antiarrhythmic agent.

The invention also provides the use of a compound of the formula (IA) or (IB), or of a pharmaceutically acceptable salt thereof, for the manufacture of a medicament for the prevention or reduction of cardiac arrhythmias.

The following Examples, in which all temperatures are in °C., illustrate the invention:

EXAMPLE 1

N-[4-(2-[N'-Methyl-N'-(4-pyridyl)amino]ethoxy)-phenyl]methanesulphonamide

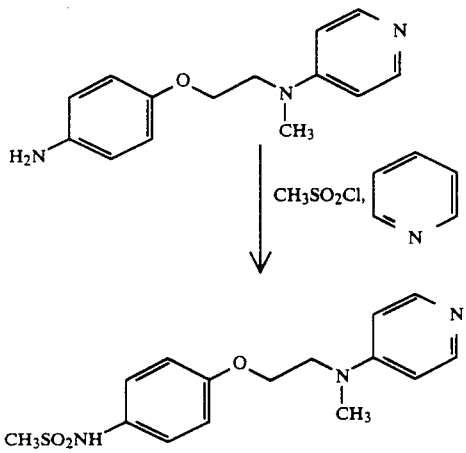

Methanesulphonyl chloride (0.151 g) was added dropwise to a stirred solution of 4-[2-(N-methyl-N-[4-pyridyl]amino)ethoxy]-benzenamine (see Preparation 1) (0.292 g) in pyridine (10 ml). The solution was stirred at room temperature for 1 hour and then evaporated. The residue was triturated with dilute sodium bicarbonate solution and the solid was filtered off, washed with water and crystallised from ethanol/water to give the title compound, (0.16 g), m.p. 134°-135°.

Analysis %: Found: C,56.12; H,6.06; N,13.08; $C_{15}H_{19}N_3O_3S$ requires: C,56.03; H,5.96; N,13.07.

EXAMPLE 2

N-[4-(N'-Methyl-N'-[2-(N''-methyl-N''-[4-pyridyl]amino)ethyl]amino)phenyl]methanesulphonamide

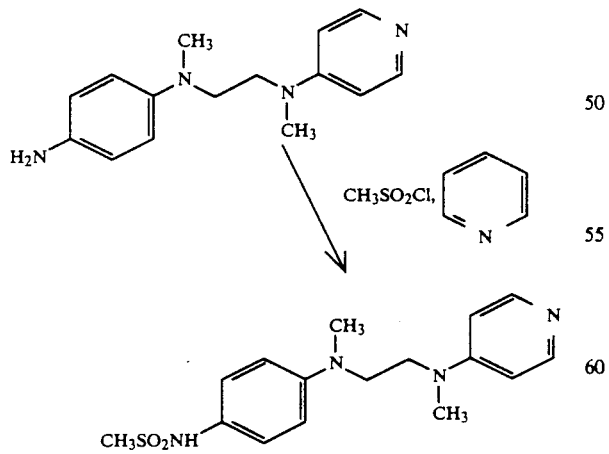

Treatment of N-(4-aminophenyl)-N,N'-dimethyl-N'-(4-pyridyl)-1,2-ethanediamine (see Preparation 2) (0.308 g) with methanesulphonyl chloride (0.151 g) in pyridine (10 ml) according to the method of Example 1 gave the title compound, (0.250 g), m.p. 199°-200° (from ethanol/water).

Analysis %: Found: C,57.41; H,6.65; N,16.76; $C_{16}H_{22}N_4O_2S$ requires: C,57.46; H,6.63; N,16.75.

EXAMPLE 3

N-[4-([1-(4-Pyridyl)piperidin-4-yl]oxy)phenyl]methanesulphonamide

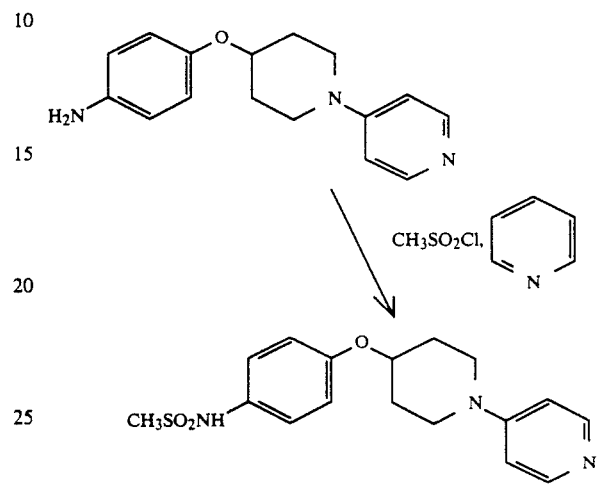

Treatment of 4-(4-aminophenoxy)-1-(4-pyridyl)-piperidine (see Preparation 3) (0.323 g) with methanesulphonyl chloride (0.151 g) in pyridine (10 ml) according to the method of Example 1 gave the title compound, (0.260 g), m.p. 191°-192° (from ethanol/water).

Analysis %: Found: C,58.80; H,6.07; N,11.82; $C_{17}H_{21}N_3O_3S$ requires: C,58.77; H,6.09; N,12.09.

EXAMPLE 4

N-[4-([1-(4-Pyridyl)piperidin-4-yl]methoxy)phenyl]methanesulphonamide

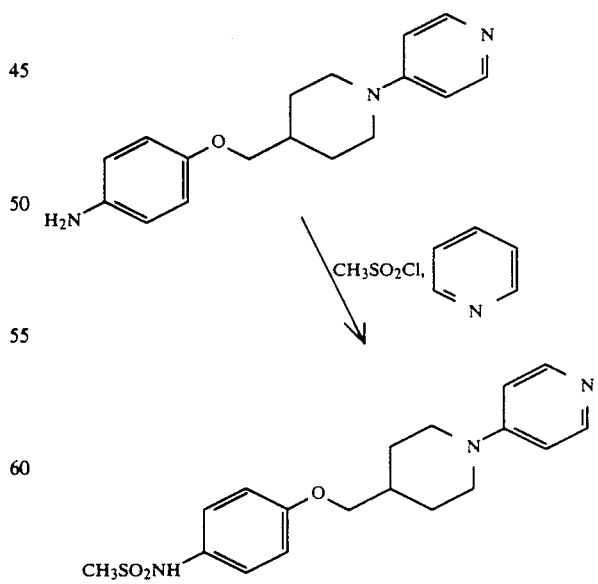

Treatment of 4-[(4-aminophenoxy)methyl]-1-[4-pyridyl]piperidine (see Preparation 4) (0.567 g) with methanesulphonyl chloride (0.263 g) in pyridine (18 ml)

according to the method of Example 1 gave the title compound, (0.50 g), m.p. 214°-215° (from ethanol).

Analysis %: Found: C,60.20; H,6.47; N,11.98; $C_{18}H_{23}N_3O_3S$ requires: C,59.81; H,6.41; N,11.63.

EXAMPLE 5

N-Methyl-N'-[4-([1-(4-pyridyl)piperidin-4-yl]methoxy)-phenyl]sulphamide

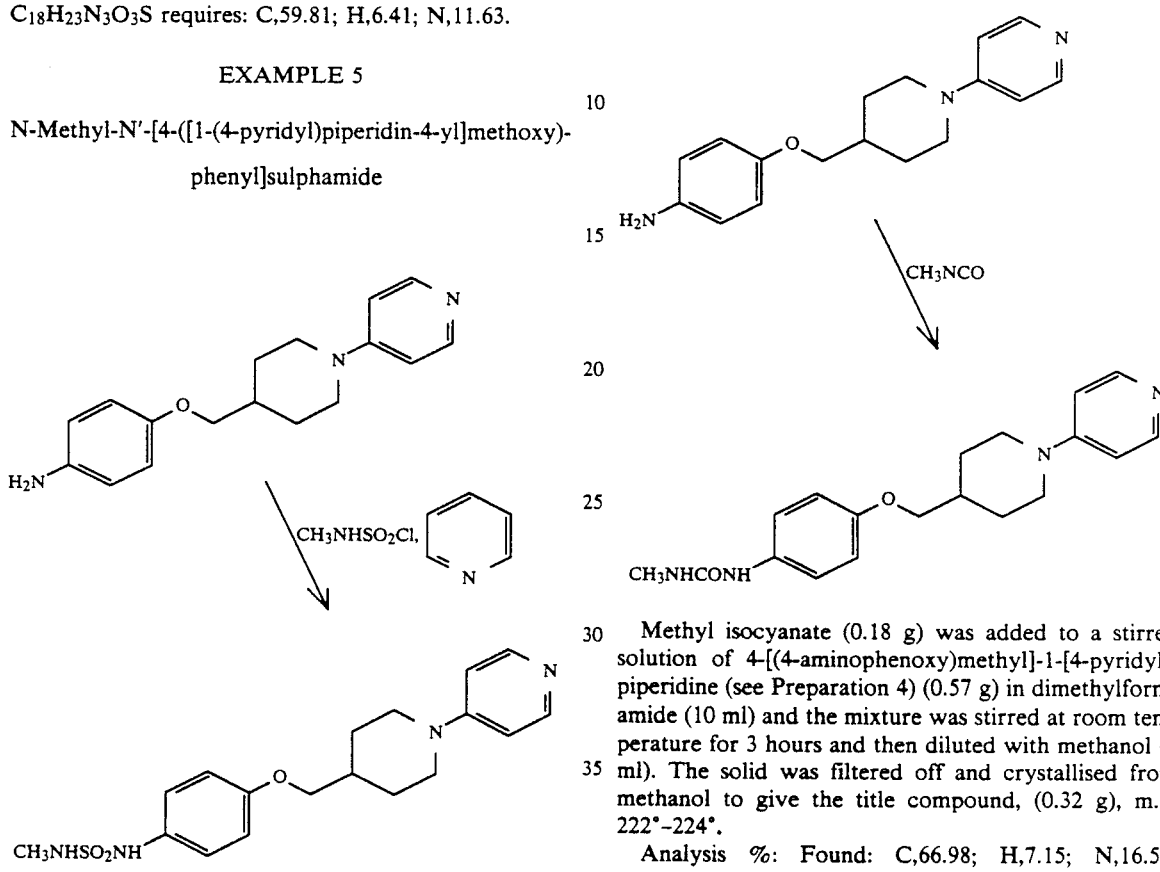

Methylsulphamoyl chloride (0.39 g) was added dropwise to a stirred solution of 4-[(4-aminophenoxy)methyl]-1-[4-pyridyl]-piperidine (see Preparation 4) (0.57 g) in pyridine (15 ml) and the mixture was stirred at room temperature for 6 hours. An additional 0.39 g of methylsulphamoyl chloride was then added and the mixture was stirred for a further 18 hours and then evaporated. The residue was partitioned between sodium bicarbonate solution and ethyl acetate. The organic layer was separated and the aqueous layer was extracted several times with ethyl acetate. The combined organic layers were washed with water, dried ($Na_2SO_4$) and evaporated. The solid residue was crystallised from ethanol to give the title compound, (0.30 g), m.p. 170.5°-172.5°.

Analysis %: Found: C,57.01; H,6.47; N,14.68; $C_{18}H_{24}N_4O_3S$ requires: C,57.42; H,6.43; N,14.88.

EXAMPLE 6

N-Methyl-N'-[4-([1-(4-pyridyl)piperidin-4-yl]methoxy)-phenyl]urea

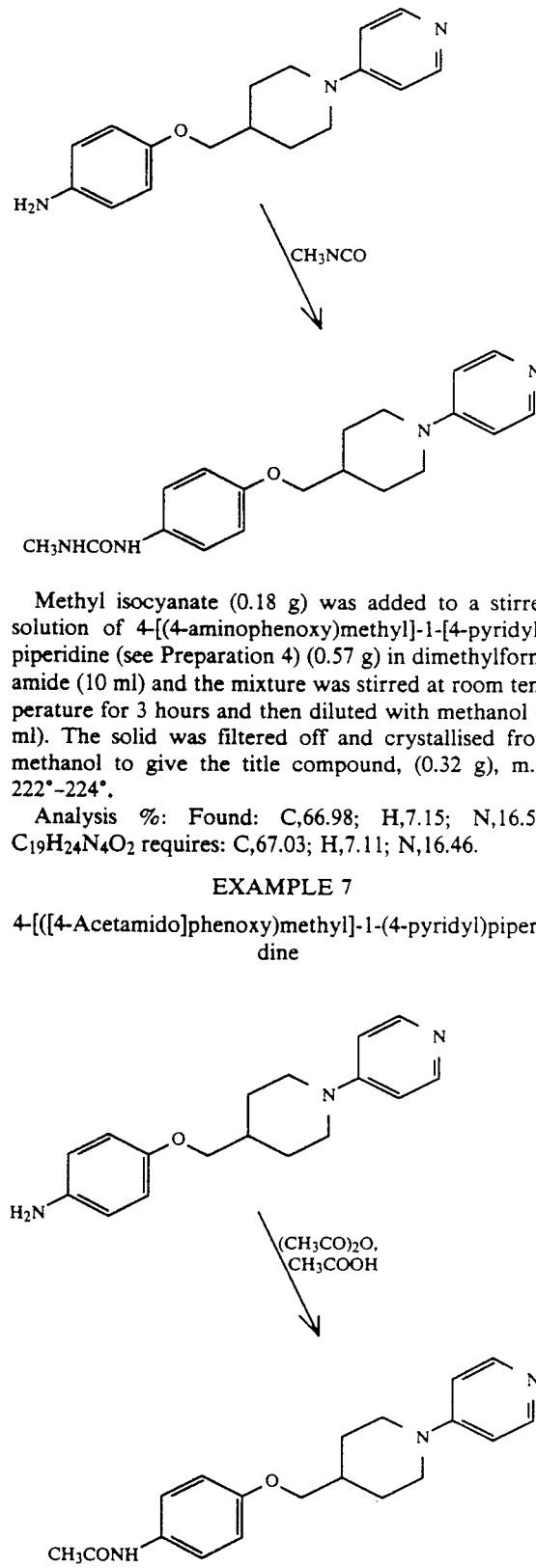

Methyl isocyanate (0.18 g) was added to a stirred solution of 4-[(4-aminophenoxy)methyl]-1-[4-pyridyl]-piperidine (see Preparation 4) (0.57 g) in dimethylformamide (10 ml) and the mixture was stirred at room temperature for 3 hours and then diluted with methanol (2 ml). The solid was filtered off and crystallised from methanol to give the title compound, (0.32 g), m.p. 222°-224°.

Analysis %: Found: C,66.98; H,7.15; N,16.58; $C_{19}H_{24}N_4O_2$ requires: C,67.03; H,7.11; N,16.46.

EXAMPLE 7

4-[([4-Acetamido]phenoxy)methyl]-1-(4-pyridyl)piperidine

A solution of 4-[(4-aminophenoxy)methyl]-1-[4-pyridyl]piperidine (see Preparation 4) (0.57 g), acetic anhydride (1 ml) and acetic acid (1 ml) was heated on a steam bath for 3 hours and then evaporated. The residue was dissolved in water (2 ml) and the solution was made basic with sodium bicarbonate solution. The solid was filtered off, washed with water, dried and then chromatographed on silica gel eluting with dichloromethane/methanol (20:1). Earlier fractions contained impurity and pure product was eluted in the later fractions. The product fractions were combined and evaporated. The solid was crystallised from methanol to give the title compound, (0.34 g), m.p. 226°–228°.

Analysis %: Found: C,70.37; H,7.24; N,12.90; C19H23N3O2 requires: C,70.13; H,7.12; N,12.91.

ration 5) (140 mg) in ethanol (50 ml) was hydrogenated at room temperature and 3.5 bar in the presence of 5% palladium on carbon until the required amount of hydrogen had been absorbed. The catalyst was filtered off and the filtrate was evaporated to give the product (120 mg), m.p. 213°–214° (from ethyl acetate/methanol).

Analysis %: Found: C,57.19; H,6.48; N,14.60; C18H24N4O3S requires: C,57.42; H,6.43; N,14.88.

The following Preparations, in which all temperatures are in °C., illustrate the preparation of the novel starting materials used in the previous Examples:

PREPARATION 1

4-[2-(N-Methyl-N-[4-pyridyl]amino)ethoxy]benzenamine

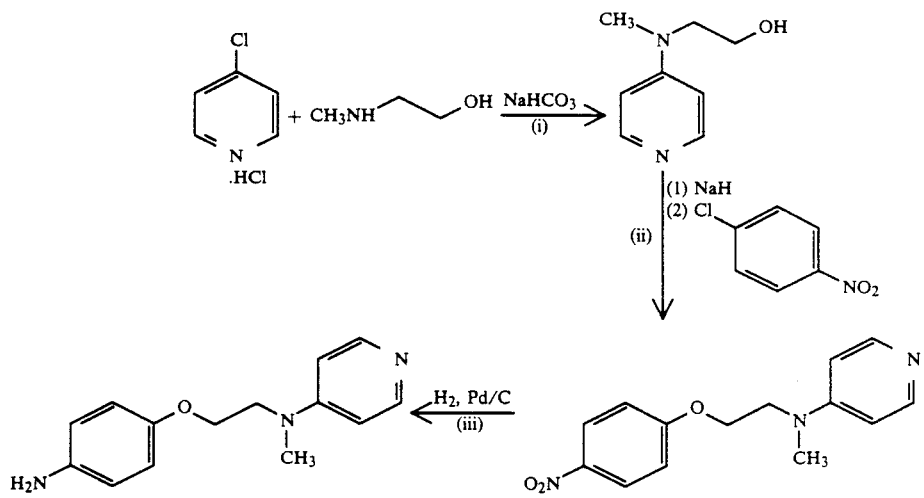

EXAMPLE 8

N-[4-([1-(4-Amino-2-pyridyl)piperidin-4-yl]methoxy)phenyl]methanesulphonamide

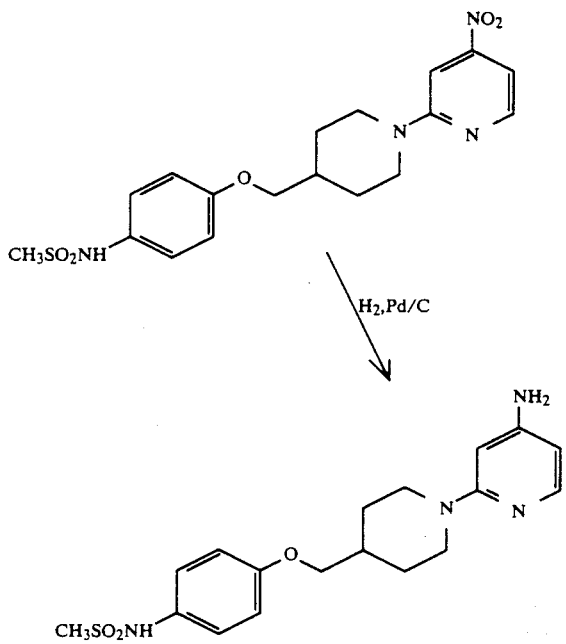

A solution of N-[4-([1-(4-nitro-2-pyridyl)piperidin-4-yl]methoxy)phenyl]methanesulphonamide (see Prepa- (i) 2-[N-Methyl-N-(4-pyridyl)amino]ethanol A mixture of 4-chloropyridine hydrochloride (4.50 g), 2-(methylamino)ethanol (2.25 g) and sodium bicarbonate (7.56 g) in isoamyl alcohol (50 ml) was heated under reflux for 70 hours and then evaporated. The residue was extracted several times with hot ethyl acetate and the combined extracts were filtered and evaporated until crystallisation commenced. The solution was allowed to cool and the solid was filtered off to give the title compound, (0.85 g), m.p. 90°–91°.

Analysis %: Found: C,63.17; H,8.02; N,18.63; C8H12N2O requires: C,63.13; H,7.95; N,18.41.

Evaporation of the filtrate and crystallisation of the residue from ethyl acetate/hexane gave a further 0.33 g of pure product.

(ii)
N-Methyl-2-(4-nitrophenoxy)-N-(4-pyridyl)ethanamine

Sodium hydride (0.16 g of a 50% dispersion in mineral oil) was added portionwise to a stirred solution of the product of part (i) (0.45 g) in dry N,N-dimethylformamide (30 ml) and the mixture was stirred at 50° for 0.3 hour and then cooled to 5°. 4-Chloronitrobenzene (0.47 g) was added portionwise and the mixture was then stirred at room temperature for 2 hours and evaporated. Water was added and the mixture was extracted several times with dichloromethane. The combined extracts were dried (Na2SO4) and evaporated to give a yellow solid which was washed with hexane to remove mineral oil. The solid was chromatographed on silica gel using dichloromethane/methanol (10:1) as eluant. The product fractions were combined and evaporated to give pure product, (0.60 g), m.p. 88°-89° (from ethyl acetate/hexane).

Analysis %: Found: C,61.20; H,5.59; N,15.29; $C_{14}H_{15}N_3O_3$ requires: C,61.53; H,5.53; N,15.38.

(iii)
4-[2-(N-Methyl-N-[4-pyridyl]amino)ethoxy]benzenamine

A solution of the product of part (ii) (0.50 g) in methanol (30 ml) was hydrogenated at room temperature and 3.5 bar in the presence of 5% palladium on carbon (50 mg) until the required amount of hydrogen had been absorbed. The catalyst was filtered off and the filtrate was evaporated to give the product, (0.43 g), m.p. 141°-142° (from ethyl acetate/hexane).

Analysis %: Found: C,69.05; H,7.31; N,17.19; $C_{14}H_{17}N_3O$ requires: C,69.11; H,7.04; N,17.27.

PREPARATION 2

N-(4-Aminophenyl)-N,N'-dimethyl-N'-(4-pyridyl)-1,2-ethanediamine

Analysis %: Found: C,65.03; H,9.20; N,25.48; $C_9H_{15}N_3$ requires: C,65.42; H,9.15; N,25.43.

(ii)
N,N'-Dimethyl-N-(4-nitrophenyl)-N'-(4-pyridyl)-1,2-ethanediamine

A mixture of the product of part (i) (0.83 g), 4-fluoronitrobenzene (0.71 g) and sodium bicarbonate (1.0 g) in N,N-dimethylformamide (20 ml) was heated at 100° with stirring for 0.5 hour and then evaporated. The residue was stirred with water (2 ml) and the insoluble material was filtered off, washed with water and dried. The solid was chromatographed on silica gel. Elution with ethyl acetate/methanol (10:1) gave, after combination and evaporation of appropriate fractions, pure product (0.60 g), m.p. 126°-127° (from ethyl acetate/hexane).

Analysis %: Found: C,62.74; H,6.31; N,19.33; $C_{15}H_{18}N_4O_2$ requires: C,62.92; H,6.34; N,19.57.

(iii)
N-(4-Aminophenyl)-N,N'-dimethyl-N'-(4-pyridyl)-1,2-ethanediamine

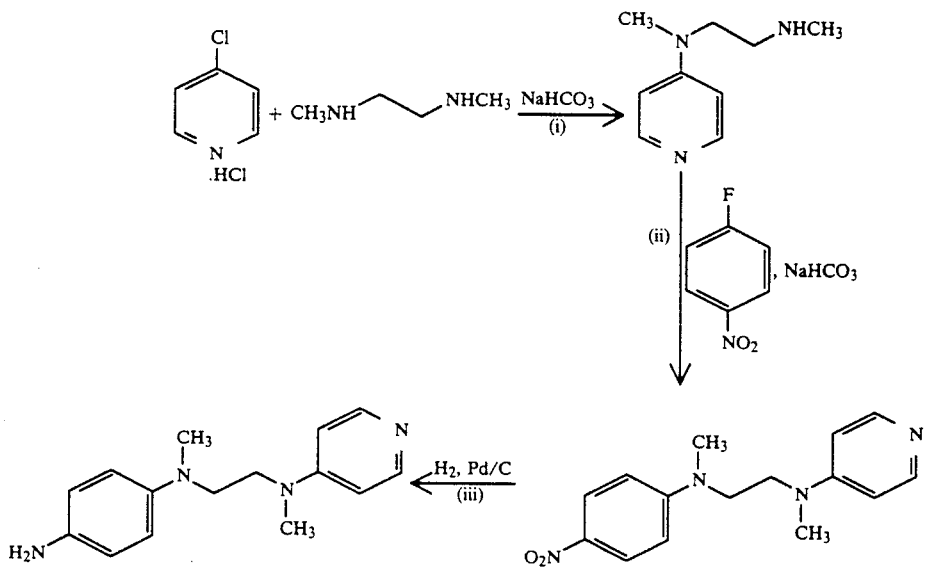

(i) N,N'-Dimethyl-N-(4-pyridyl)-1,2-ethanediamine

A mixture of 4-chloropyridine hydrochloride (15.0 g), N,N'-dimethyl-1,2-ethanediamine (22.0 g) and sodium bicarbonate (25.20 g) in isoamyl alcohol (100 ml) was heated under reflux for 48 hours and then evaporated. The residue was extracted several times with hot dichloromethane and the combined extracts were filtered and evaporated. The residue was distilled to give the product (8.30 g), b.p. 168°-172° @ 15 mm.

A solution of the product of part (ii) (0.50 g) in methanol (50 ml) was hydrogenated at room temperature and 3.5 bar in the presence of 5% palladium on carbon (50 mg) until the required amount of hydrogen had been absorbed. The catalyst was filtered off and the filtrate was evaporated to give the title compound (0.45 g) as a gum which was used without further purification.

PREPARATION 3

4-(4-Aminophenoxy)-1-(4-pyridyl)piperidine

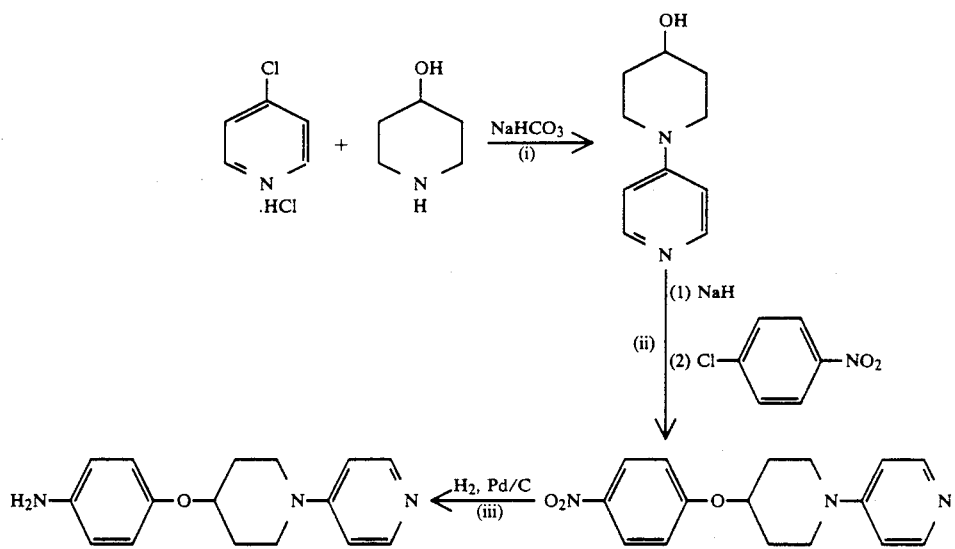

(i) 1-(4-Pyridyl)-4-piperidinol

A mixture of 4-chloropyridine hydrochloride (7.50 g), 4-hydroxypiperidine (5.06 g) and sodium bicarbonate (10.1 g) in isoamyl alcohol (60 ml) was heated under reflux with stirring for 60 hours and then evaporated. The residue was extracted several times with a boiling mixture of ethyl acetate/methanol (10:1) and the combined extracts were filtered and evaporated. The residue was sublimed at 120°-150° and 0.2 mm pressure to give the pure product, (7.30 g), m.p. 155°-156°.

Analysis %: Found: C,67.21; H,7.77; N,15.77; $C_{10}H_{14}N_2O$ requires: C,67.38; H,7.92; N,15.72.

(ii) 4-(4-Nitrophenoxy)-1-(4-pyridyl)piperidine

Treatment of the product of part (i) (1.78 g) with sodium hydride (0.53 g of a 50% dispersion in mineral oil) followed by 4-chloronitrobenzene according to the method of Preparation 1, part (ii) gave the title compound, (1.45 g), m.p. 142°-143° (from ethyl acetate/hexane).

Analysis %: Found: C,64.24; H,5.68; N,14.05; $C_{16}H_{17}N_3O_3$ requires: C,64.20; H,5.72; N,14.04.

(iii) 4-(4-Aminophenoxy)-1-(4-pyridyl)piperidine

Hydrogenation of the product of part (ii) (1.10 g) according to the method of Preparation 1, part (iii) gave the title compound, (0.99 g), m.p. 209°-210° (from ethyl acetate/ethanol).

Analysis %: Found: C,71.59; H,7.23; N,15.52; $C_{16}H_{19}N_3O$ requires: C,71.34; H,7.11; N,15.60.

PREPARATION 4

4-[(4-Aminophenoxy)methyl]-1-[4-pyridyl]piperidine

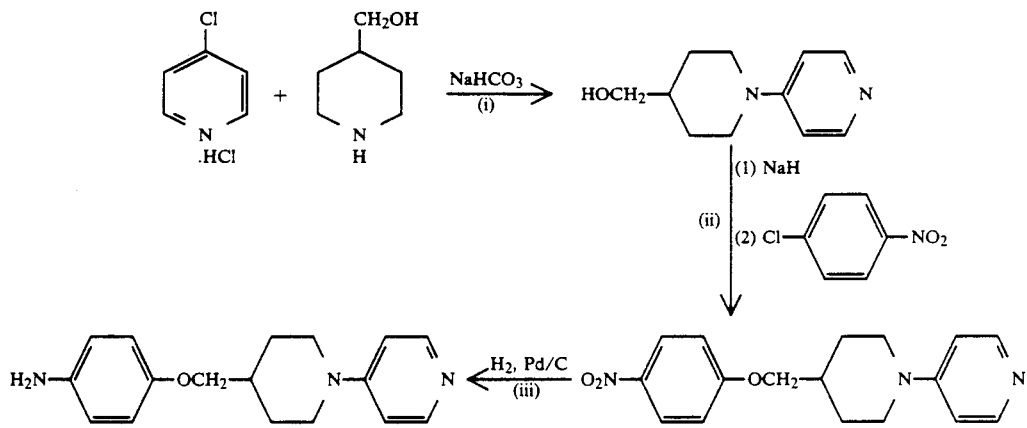

(i) 1-(4-Pyridyl)-4-piperidinemethanol

Treatment of 4-chloropyridine hydrochloride (10.5 g) with 4-piperidinemethanol (8.06 g) and sodium bicarbonate (13.44 g) in isoamyl alcohol (100 ml) according to the method of Preparation 3, part (i), followed by purification by sublimation, gave the title compound, (5.35 g), m.p. 183°-185°.

Analysis %: Found: C,68.62; H,8.37; N,14.58; $C_{11}H_{16}N_2O$ requires: C,68.71; H,8.39; N,14.57.

(ii) 4-[(4-Nitrophenoxy)methyl]-1-[4-pyridyl]piperidine

Treatment of the product of part (i) (1.92 g) with sodium hydride (0.53 g of a 50% dispersion in mineral oil) followed by 4-chloronitrobenzene (1.58 g) according to the method of Preparation 1, part (ii) gave the title compound (1.75 g), m.p. 119°-120° (from ethyl acetate/hexane).

Analysis %: Found: C,65.16; H,6.10; N,13.40; $C_{17}H_{19}N_3O_3$ requires: C,65.16; H,6.11; N,13.41.

(iii) 4-[(4-Aminophenoxy)methyl]-1-[4-pyridyl]piperidine

Hydrogenation of the product of part (ii) (1.50 g) according to the method of Preparation 1, part (iii) gave the title compound, (1.30 g), m.p. 207°-209° (from ethanol).

Analysis %: Found: C,72.19; H,7.49; N,14.58; $C_{17}H_{21}N_3O$ requires: C,72.05; H,7.47; N,14.83.

PREPARATION 5

N-[4-([1-(4-Nitro-2-pyridyl)piperidin-4-yl]methoxy)-phenyl]methanesulphonamide

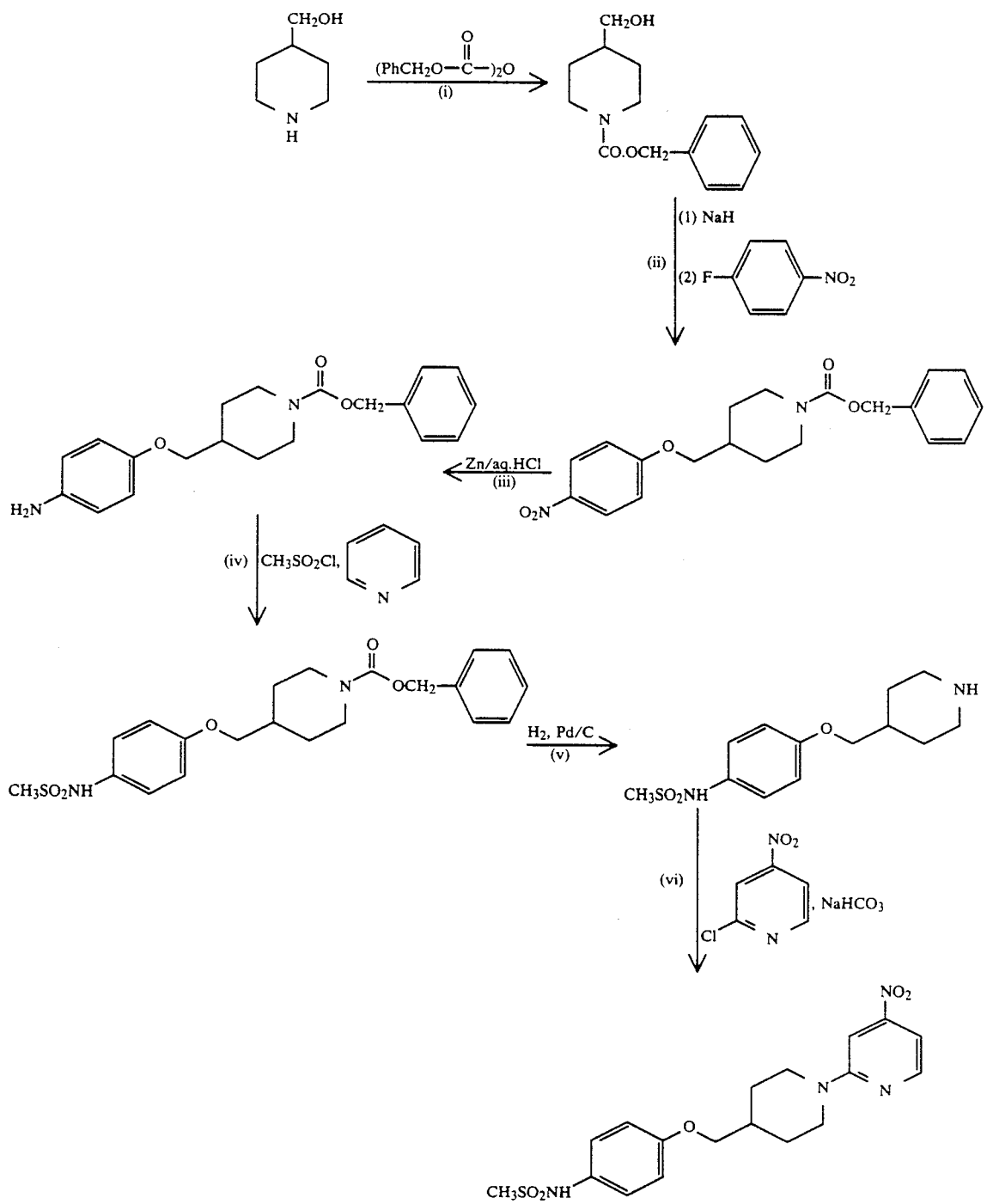

(i) 1-(Benzyloxycarbonyl)-4-piperidinemethanol

Dibenzyldicarbonate (28.6 g) was added portionwise to a stirred solution of 4-piperidinemethanol (11.3 g) in 1,4-dioxane (50 ml) and water (50 ml). The solution was stirred for 1 hour and then evaporated. Water was added to the residue and the mixture was extracted several times with ethyl acetate. The combined extracts were washed with water, dried (MgSO₄) and evaporated to give an oil which was chromatographed on silica gel, eluting with ether. Earlier fractions contained impurity and the pure product was eluted in the later fractions. The product fractions were combined and evaporated to give a viscous oil, (18.45 g), which was used without further purification.

(ii)
1-(Benzyloxycarbonyl)-4-[(4-nitrophenoxy)methyl]-piperidine

Sodium hydride (3.36 g of a 50% dispersion in mineral oil) was added portionwise to a stirred solution of the product of part (i) (17.43 g) in dry tetrahydrofuran (200 ml) and the mixture was stirred at room temperature for 1 hour. 4-Fluoronitrobenzene (9.87 g) was added dropwise and the mixture was stirred for a further 18 hours and then evaporated. Water was added to the residue and the mixture was extracted several times with dichloromethane. The combined extracts were washed with water, dried (MgSO4) and evaporated to give an oil which solidified on trituration with ether. The solid was filtered off, washed with a little ether and crystallised from ethyl acetate/hexane to give the product, (13.51 g), m.p. 121°-122°.

Analysis %: Found: C,64.40; H,6.07; N,7.24; $C_{20}H_{22}N_2O_5$ requires: C,64.85; H,5.99; N,7.56.

(iii)
4-[(4-Aminophenoxy)methyl]-1-(benzyloxycarbonyl)-piperidine

A solution of the product of part (ii) (10.0 g) in ethanol (400 ml) and 2N hydrochloric acid (200 ml) was heated to reflux with stirring. Zinc dust (8.80 g) was added at such a rate that the ensuing reaction was not too vigorous. The mixture was heated under reflux for 0.25 hour and then cooled and filtered. The filtrate was made basic with 0.88 ammonia solution and diluted with a large volume of water. The mixture was extracted several times with ethyl acetate and the combined extracts were washed with water and dried (Na2SO4). Evaporation of the solvent gave an oil which was chromatographed on silica gel, eluting with dichloromethane. Earlier fractions contained impurity and the pure product was eluted in the later fractions. The product fractions were combined and evaporated to give an oil, (5.50 g). The product darkened rapidly and was used directly without further purification.

(iv)
N-[4-([1-(Benzyloxycarbonyl)piperidin-4-yl]methoxy)-phenyl]methanesulphonamide Methanesulphonyl chloride (1.91 g) was added to a stirred solution of the product of part (iii) (5.15 g) in pyridine (50 ml) at 0°. The solution was stirred at room temperature for 18 hours and then evaporated. The residue was treated with aqueous sodium bicarbonate solution and the mixture was extracted several times with ethyl acetate. The combined extracts were washed with water, dried (Na2SO4) and evaporated. The residue was crystallised from ethyl acetate/hexane to give the title compound, (5.17 g), m.p. 150°-151°.

Analysis %: Found: C,60.27; H,6.34; N,6.59; $C_{21}H_{26}N_2O_5S$ requires: C,60.27; H,6.26; N,6.69;

(v)
N-[4-([Piperidin-4-yl]methoxy)phenyl]methanesulphonamide

A solution of the product of part (iv) (0.15 g) in ethanol was hydrogenated at 50° and 3.5 bar in the presence of 5% palladium on carbon until the required amount of hydrogen had been absorbed. The catalyst was filtered off and washed several times with hot ethanol. The combined filtrate and washings were evaporated to give the product, (0.10 g), m.p. 180°-183°, which was used without further purification.

(vi)
N-[4-([1-(4-Nitro-2-pyridyl)piperidin-4-yl]methoxy)-phenyl]methanesulphonamide A mixture of the product of part (v) (0.50 g), 2-chloro-4-nitropyridine (0.28 g) and sodium bicarbonate (1.00 g) in n-butanol (20 ml) was heated under reflux with stirring for 18 hours. The mixture was cooled, filtered, and the residue was washed with ethanol. The combined filtrate and washings were evaporated to give a gum which was chromatographed on silica gel eluting with ether. Earlier fractions gave impurity and the pure product was eluted in the later fractions. The product fractions were combined and evaporated to give the product, (0.21 g), m.p. 183.5°-184.5° (from ethanol).

Analysis %: Found: C,53.55; H,5.67; N,13.46; $C_{18}H_{22}N_4O_5S$ requires: C,53.19; H,5.46; N,13.79.

We claim:
1. A compound of the formula:

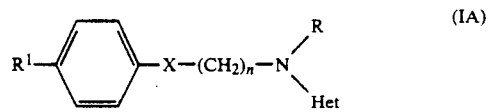

or a pharmaceutically acceptable salt thereof, wherein
X is —O— or —N(C1-C4 alkyl)—;
R is C1-C4 alkyl;
R1 is R2SO2NH— or R2CONH— where R2 is C1-C4 alkyl, C3-C7 cycloalkyl or R3R4N— where R3 and R4 are each independently hydrogen or C1-C4 alkyl;
"Het" is a 2-, 3- or 4-pyridyl group optionally substituted by one or two substituents each independently selected from amino and C1-C4 alkyl; and
n is an integer of from two to four, inclusive.
2. A compound as claimed in claim 1 of the formula (IA).
3. A compound as claimed in claim 1 wherein "Het" is 2-, 3- or 4-pyridyl optionally substituted by one or two substituents each independently selected from amino and C1-C4 alkyl.
4. A compound as claimed in claim 3 wherein "Het" is unsubstituted 4-pyridyl.
5. A compound as claimed in claim 1 wherein each C1-C4 alkyl group is methyl.
6. A compound as claimed in claim 1 wherein R1 is CH3SO2NH—.
7. A compound as claimed in claim 2 wherein X is —O— or —N(CH3)— and n is two.
8. A compound as claimed in claim 5 wherein R is methyl, R1 is CH3SO2NH— and "Het" is unsubstituted 4-pyridyl.
9. A compound as claimed in claim 6 wherein X is —N(CH3)—, which is N—[4-(N'-methyl-N'-[2-(N''-methyl-N''-[4-pyridyl]amino)ethyl]amino)phenyl]methanesulphonamide.
10. An anti-arrhythmic pharmaceutical composition comprising a pharmaceutically acceptable carrier or diluent and an effective anti-arrhythmic amount of a compound as claimed in claim 1.
11. A method for preventing or reducing cardiac arrhythmias in the treatment of a mammal in need of such treatment, which comprises administering to said mammal an effective anti-arrhythmic amount of a compound as claimed in claim 1.

* * * * *